United States Patent
Gad et al.

(10) Patent No.: US 10,494,532 B2
(45) Date of Patent: *Dec. 3, 2019

(54) METHOD OF PREVENTING OR TREATING ORAL INFECTIONS USING ZIRCONIA AUTOPOLYMERIZABLE RESINS

(71) Applicant: Imam Abdulrahman Bin Faisal University, Dammam (SA)

(72) Inventors: Mohammed Moustafa Ahmed Gad, Dammam (SA); Ahmad M. Al-Thobity, Dammam (SA); Suliman S. Shahin, Dammam (SA)

(73) Assignee: Imam Abulrahman Bin Faisal University, Dammam (SA)

(*) Notice: Subject to any disclaimer, the term of this patent is extended or adjusted under 35 U.S.C. 154(b) by 64 days.

This patent is subject to a terminal disclaimer.

(21) Appl. No.: 15/840,267

(22) Filed: Dec. 13, 2017

(65) Prior Publication Data

US 2018/0325782 A1   Nov. 15, 2018

Related U.S. Application Data

(60) Provisional application No. 62/503,706, filed on May 9, 2017.

(51) Int. Cl.

| | |
|---|---|
| *A61K 6/00* | (2006.01) |
| *A61C 13/00* | (2006.01) |
| *C08L 33/12* | (2006.01) |
| *B29C 73/02* | (2006.01) |
| *C08K 3/22* | (2006.01) |
| *C09D 7/62* | (2018.01) |
| *A61K 6/083* | (2006.01) |
| *C09D 4/00* | (2006.01) |
| *C09D 7/40* | (2018.01) |
| *C09D 5/03* | (2006.01) |
| *C09D 1/00* | (2006.01) |
| *A61P 1/02* | (2006.01) |
| *A61K 33/30* | (2006.01) |
| *A61K 47/32* | (2006.01) |
| *B29K 105/16* | (2006.01) |
| *C08K 9/06* | (2006.01) |
| *B29K 33/00* | (2006.01) |
| *B29K 509/02* | (2006.01) |

(52) U.S. Cl.
CPC ............ *C09D 7/62* (2018.01); *A61C 13/0024* (2013.01); *A61K 6/0008* (2013.01); *A61K 6/0026* (2013.01); *A61K 6/0073* (2013.01); *A61K 6/0835* (2013.01); *A61K 33/30* (2013.01); *A61K 47/32* (2013.01); *A61P 1/02* (2018.01); *C08L 33/12* (2013.01); *C09D 1/00* (2013.01); *C09D 4/00* (2013.01); *C09D 5/03* (2013.01); *C09D 7/66* (2018.01); *C09D 7/67* (2018.01); *C09D 7/68* (2018.01); *B29C 73/02* (2013.01); *B29K 2033/12* (2013.01); *B29K 2105/162* (2013.01); *B29K 2509/02* (2013.01); *C08K 3/22* (2013.01); *C08K 9/06* (2013.01); *C08K 2003/2244* (2013.01)

(58) Field of Classification Search
None
See application file for complete search history.

(56) References Cited

U.S. PATENT DOCUMENTS

2016/0096956 A1* 4/2016 Boday .................... C08L 65/00
                                                                   525/112

FOREIGN PATENT DOCUMENTS

| CN | 104287976 B | 5/2017 |
|---|---|---|
| WO | WO 99/42079 A2 | 8/1999 |
| WO | WO 2016/130985 A1 | 8/2012 |

OTHER PUBLICATIONS

MM Gad, A Rahoma, AM Al-Thobity, AS ArRejaie. "Influence of incorporation of ZrO2 nanoparticles on the repair strength of polymethyl methacrylate denture bases." International Journal of Nanomedicine, vol. 11, 2016, pp. 5633-5643. (Year: 2016).*
HK Hameed, HA Rahman. "The effect of addition nano particle ZrO2 on some properties of autoclave processed heat cure acrylic denture base material." Journal of the Baghdad College of Dentistry, vol. 27(1), Mar. 2015, pp. 32-39. (Year: 2015).*
W Yu, X Wang, Q Tang, M Guo, J Zhao. "Reinforcement of denture base PMMA with ZrO2 nanotubes." Journal of the Mechanical Behavior of Biomedical Materials, vol. 32, 2014, pp. 192-197. (Year: 2014).*
SL Jangra, K Stalin, N Dilbaghi, S Kumar, J Tawale, SP Singh, R Pasricha. "Antimicrobial Activity of Zirconia (ZrO2) Nanoparticles and Zirconium Complexes." Journal of Nanoscience and Nanotechnology, vol. 12, 2012, pp. 7105-7112. (Year: 2012).*
MA Ahmed, MI Ebrahim. "Effect of Zirconium Oxide Nano-Fillers Addition on the Flexural Strength, Fracture Toughness, and Hardness of Heat-Polymerized Acrylic Resin." World Journal of Nano Science and Engineering, vol. 4, 2014, pp. 50-57. (Year: 2014).*
Cássio do Nascimento, et al., "In vivo evaluation of *Candida* spp. adhesion on titanium or zirconia abutment surfaces", Archives of Oral Biology, vol. 58, No. 7, 2013, pp. 853-661.
Achut R. Devarhubli, et al., "Surface Adherence of *Candida albicans* to Different Poiymethyl Methacrylate Resin Denture Base Materials", World Journal of Dentistry, vol. 2, No, 3, Jul.-Sep. 2011, pp. 237-242.
Grzegorz Chladek, et al., "Effect of Storage in Distilled Water for Three Months on the Antimicrobial Properties of Poly(methyl methacrylate) Denture Base Material Doped with Inorganic Filler", Materials, vol. 9, No. 328, 2016, pp. 1-17.
Mohammed M. Gad, et al., "In Vitro Investigation of *Candida albicans* Adhesion to Repair Resin Modified with Nano-Zirconia Filler", Conference Paper, https://www.researchgate.net/publication/316286146_In_Vitro_Investigation_of_Candida_Albicans_Adhesion_to_Repair_Resin_Modified_with_Nano-Zirconia_Filler, Apr. 2017, 1 page.

* cited by examiner

*Primary Examiner* — Isaac Shomer
(74) *Attorney, Agent, or Firm* — Oblon, McClelland, Maier & Neustadt, L.L.P.

(57) ABSTRACT

A method of preventing or treating an oral disease by reducing adhesion of microorganisms, e.g. *Candida albicans*, to dental appliances fabricated and/or repaired by an autopolymerizing acrylic reinforcement resin comprising zirconium dioxide nanoparticles.

11 Claims, 8 Drawing Sheets

METHOD OF PREVENTING OR TREATING ORAL INFECTIONS USING ZIRCONIA AUTOPOLYMERIZABLE RESINS

CROSS REFERENCE TO RELATED APPLICATIONS

This application claims the benefit of priority of U.S. Provisional Application No. 62/503,706 filed May 9, 2017, the entire contents of which are herein incorporated by reference.

STATEMENT REGARDING PRIOR DISCLOSURE BY THE INVENTORS

Aspects of this technology are described in articles titled "Inhibitory effect of zirconium oxide nanoparticles on *Candida albicans* adhesion to repaired polymethyl methacrylate denture bases and interim removable prostheses: a new approach for denture stomatitis prevention" published in *International Journal of Nanomedicine*, 2017, 12, 5409-5419, on Jul. 28, 2017, "The reinforcement effect of nano-zirconia on the transverse strength of repaired acrylic denture base" published in *International Journal of Dentistry*, 2016, vol. 2016, Article ID 7094056, on May 9, 2017, and "Influence of incorporation of $ZrO_2$ nanoparticles on the repair strength of polymethyl methacrylate denture bases" published in *International Journal of Nanomedicine*, 2016, 11, 5633-5643, on Oct. 27, 2016, which are incorporated herein by reference in their entirety.

BACKGROUND OF THE INVENTION

Technical Field

The present invention relates to a method for reducing adhesion of microorganisms to dental appliances fabricated and/or repaired by an autopolymerizing acrylic reinforcement resin comprising zirconium dioxide nanoparticles, and to dental appliances coated with or containing the cured resin.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Polymethyl methacrylate (PMMA) is a material used for fabrication of complete and partial removable dentures. However, surface roughness and apparent porosity of PMMA which can act as a reservoir for microorganisms (Zomorodian K, Haghighi N N, Rajaee N, et al. Assessment of *Candida* species colonization and denture-related stomatitis in complete denture wearers. *Med Mycol.* 2011, 49(2), 208-211; and Pattanaik S. Denture stomatitis: a literature review. *J Indian Acad Oral Med Radial.* 2010, 22(3), 136-140, each incorporated herein by reference in their entirety) limit its applications in many clinical and prosthodontic practices. Moreover, improper denture hygiene causes surface scratches, debris accumulation, and biofilm formation, which contribute to inflammatory changes in the neighboring mucosa and cause denture stomatitis (DS) (Budtz-Jorgensen E. Oral mucosal lesions associated with the wearing of removable dentures. *J Oral Pathol.* 1981, 10(2), 65-80, incorporated herein by reference in its entirety).

DS, a disease associated with *Candida albicans*, is a common and repetitive problem for complete-denture wearers (Gendreau L, Loewy Z. Epidemiology and etiology of denture stomatitis. *J Prosthodont.* 2011, 20(4), 251-260; von Fraunhofer J A, Loewy Z G. Factors involved in microbial colonization of oral prostheses. *Gen Dent.* 2009, 57(2), 136-143; Ferreira M A, Pereira-Cenci T, Rodrigues L M, Rodrigues-Garcia R C, Del Bel Cury A A. Efficacy of denture cleansers on denture liners contaminated with *Candida* species. *Clin Oral Investig.* 2009, 13(2), 237-242, each incorporated herein by reference in their entirety). The initial attachment and adhesion of *C. albicans* to the intaglio surface of a denture base results in the colonization and pathogenesis that causes DS (Vasilas A, Molina L, Hoffman M, Haidaris C G. The influence of morphological variation on *Candida albicans* adhesion to denture acrylic in vitro. *Arch Oral Biol.* 1992, 37(8), 613-622, incorporated herein by reference in its entirety). Barbeau et al (Barbeau J, Seguin J, Goulet J P, et al. Reassessing the presence of *Candida albicans* in denture-related stomatitis. *Oral Surg Oral Med Oral Pathol Oral Radiol Endod.* 2003, 95(1), 51-59, incorporated herein by reference in its entirety) discloses that prevention of DS should start from essential plaque control through patient education on thorough daily denture cleaning. It was stated that mechanical cleaning methods are inadequate to reduce microorganisms on denture surfaces (Dills S S, Olshan A M, Goldner S, Brogdon C. Comparison of the antimicrobial capability of an abrasive paste and chemical-soak denture cleaners. *J Prosthet Dent.* 1988, 60(4), 467-470, incorporated herein by reference in its entirety). Therefore, there is a need to develop more effective methods to reduce *C. albicans* adhesion and subsequent colonization on a denture base (Izumida F E, Moffa E B, Vergani C E, Machado A L, Jorge J H, Giampaolo E T. In vitro evaluation of adherence of *Candida albicans, Candida glabrata,* and *Streptococcus mutans* to an acrylic resin modified by experimental coatings. *Biofouling.* 2014, 30(5), 525-533; Ali A A, Alharbi F A, Suresh C S. Effectiveness of coating acrylic resin dentures on the *Candida* adhesion. *J Prosthodont.* 2013, 22(6), 445-450; Yodmongkol S, Chantarachindawong R, Thaweboon S, Thaweboon B, Amornsakchai T, Srikhirin T. The effects of silane-$SiO_2$ nanocomposite films on *Candida albicans* adhesion and the surface and physical properties of acrylic resin denture base material. *J Prosthet Dent.* 2014, 112(6), 1530-1538; Queiroz J C, Fissmer S F, Koga-Ito C Y, et al. Effect of diamond-like carbon thin film coated acrylic resin on *Candida albicans* biofilmr formation. *J Prosthodont.* 2013, 22(6), 451-455; and Nawasrah A, AlNimr A, Ali A A. Antifungal effect of henna against *Candida albicans* adhered to acrylic resin as a possible method for prevention of denture stomatitis. *Int J Environ Res Public Health.* 2016, 13(5), 520, each incorporated herein by reference in their entirety).

Denture base fracture is a recurring problem among denture wearers, which subsequently requires denture replacement or repair (Faot F, da Silva W J, da Rosa R S, Del Bel Cury A A, Garcia R C. Strength of denture base resins repaired with auto- and visible light-polymerized materials. *J Prosthodont.* 2009, 18(6), 496-502; Beyli M S, von Fraunhofer J A. Repair of fractured acrylic resin. *J Prosthet Dent.* 1980, 44(5), 497-503; Polyzois G L, Handley R W, Stafford G D. Repair strength of denture base resins using various methods. *Eur J Prosthodont Restor Dent.* 1995, 34(4), 183-186; Alkurt M, Yesil Duymus Z, Gundogdu M.

Effect of repair resin type and surface treatment on the repair strength of heat-polymerized denture base resin. *J Prosthet Dent.* 2014, 111(1), 71-78; Seo R S, Neppelenbroek K H, Filho J N. Factors affecting the strength of denture repairs. *J Prosthodont.* 2007, 16(4), 302-310; Vallittu P K. The effect of surface treatment of denture acrylic resin on the residual monomer content and its release into water. *Acta Odontol Scand.* 1996, 54(3), 188-192; and Beyli M S, von Fraunhofer J A. An analysis of causes of fracture of acrylic resin dentures. *J Prosthet Dent.* 1981, 46(3), 238-241, each incorporated herein by reference in their entirety). Since denture fabrication is costly and time-consuming, denture repair is usually a preferred option. To restore the original shape and strength, there are several repair resins available with enhanced technical and clinical properties. Because of its ease of handling and quick processing time, cold-cured acrylic resin is the most popular denture repair material, as it saves chairside time and patient wait time (ArioliFilho J N, Butignon L E, Pereira Rde P, Lucas M G, MolloFde A J. Flexural strength of acrylic resin repairs processed by different methods: water bath, microwave energy and chemical polymerization. *J App Oral Sci.* 2011, 19(3), 249-253, incorporated herein by reference in its entirety). Unfortunately, the low surface area and porosity of cold-cured repair resin increase its susceptibility to *Candida* adhesion (Kulak Y, Arikan A, Kazazoglu E. Existence of *Candida albicans* and microorganisms in denture stomatitis patients. *J Oral Rehabil.* 1997, 24(10), 788-790; and Radford D R, Sweet S P, Challacombe S J, Walter J D. Adherence of *Candida albicans* to denture-base materials with different surface finishes. *J Dent.* 1998, 26(7), 577-583, each incorporated herein by reference in their entirety). Sahin et al tested heat-polymerized, cold-cured, microwave-cured, and light-cured repair materials for their flexural strength and *Candida* adhesion, and found that the repair materials were highly susceptible to *C. albicans* adhesion. The flexural strengths of these materials were not satisfactory for prosthodontic practice (Sahin C, Ergin A, Ayylldiz S, Uzun G. Evaluation of flexural strength and *Candida albicans* adhesion of an acrylic resin repaired with 4 different resin materials. *Clin Dent Res.* 2012, 36(2), 10-14, incorporated herein by reference in its entirety). Moreover, repaired dentures, which are made of two different resins including the heat-polymerized old denture base and the cold-cured repair resin, together with junctions between the two resins increase their susceptibility to *Candida* adhesion. Therefore, various studies have investigated the effect of reinforcement materials and surface treatment on the physical properties of repaired dentures.

Some applications of cold-cured acrylic resin include interim removable prostheses, maxillofacial prostheses, orthodontic removable appliances, and implant-supported fixed interim prostheses (Ferro K J, Morgano S M, Driscoll C F, et al. The glossary of prosthodontic terms. Ninth edition. The academy of prosthodontics. *J. Prosthet Dent.* 2017, 117, 1-105; Higginbottom F, Belser U, Jones J, Keith S. Prosthetic management of implants in the esthetic zone. *Int J Oral Maxillofac Implants.* 2004, 19(suppl), 62-72; Al-Thobity A M. Fabrication of an implant-supported fixed interim prosthesis using a duplicate denture: an alternative technique. *J Prosthodont.* Epub 2016; and Alfonso C, Toothacker R W, Wright R F, White G S. A technique to create appropriate abutment tooth contours for removable partial dentures. *J Prosthodont.* 1999, 8(4), 273-275, each incorporated herein by reference in their entirety). Despite wide applications of cold-cured acrylic resin as interim prostheses, it has physical and mechanical limitations that should be addressed.

Nano-sized materials have contributed tremendously to the advancement of nanomedicine and biomedical sciences due to their brilliant physical, chemical and biological properties (Gu F X, Karnik R, Wang A Z, et al. Targeted nanoparticles for cancer therapy. *Nano Today.* 2007, 3, 14-21; Ki-Young N, Cheong-Hee L, Chul-Jae L. Antifungal and physical characteristics of modified denture base acrylic incorporated with silver nanoparticles. *Gerodontology.* 2012, 29(2), e413-e419; Matsuura T, Abe Y, Sato Y, Okamoto K, Ueshige M, Akagawa Y. Prolonged antimicrobial effect of tissue conditioners containing silver-zeolite. *J Dent.* 1997, 25(5), 373-377; and Veeraapandian S, Sawant S N, Doble M. Antibacterial and antioxidant activity of protein capped silver and gold nanoparticles synthesized with *Escherichia coli*. *J Biomed Nanotechnol.* 2012, 8(1), 140-148, each incorporated herein by reference in their entirety). Recently, much attention has been directed toward the incorporation of nanoparticles into PMMA to improve its properties. Nano-$ZrO_2$ is broadly used to reinforce and improve the properties of PMMA. It has been reported that the addition of nano-$ZrO_2$ significantly improved the physical and mechanical properties of PMMA/$ZrO_2$ nanocomposite (Gad M M, Fouda S M, Al-Harbi F A, Näpänkangas R, Raustia A. PMMA denture base material enhancement: a review of fiber, filler, and nano-filler addition. *Int J Nanomedicine.* 2017, 12, 3801-3812; Ayad N M, Badawi M F, Fatah A A. Effect of reinforcement of high-impact acrylic resin with zirconia on some physical and mechanical properties. *Rev Cli'n Pesq Odontol.* 2008, 4(3), 145-151; Mallineni S K, Nuvvula S, Matinlinna J P, Yiu C K, King N M. Biocompatibility of various dental materials in contemporary dentistry: a narrative insight. *J Investig Clin Dent.* 2013, 4(1), 9-19; and Seabra A B, Durán N. Nanotoxicology of metal oxide nanoparticles. *Metals.* 2015, 5(2), 934-975, each incorporated herein by reference in their entirety). Slight improvement on the surface properties (increase in hardness and decrease in apparent porosity) was seen by increasing the concentration of nano-$ZrO_2$ (Hameed H K, Abdul Rahman H. The effect of addition nanoparticle $ZrO_2$ on some properties of autoclave processed heat cures acrylic denture base material. *J Bagh Coll Dent.* 2015, 27(1), 32-39, incorporated herein by reference in its entirety). Recently, Gad et al (Gad M, ArRejaie A S, Abdel-Halim M S, Rahoma A. The reinforcement effect of nano-zirconia, on the transverse strength of repaired acrylic denture base. *Int J Dent.* 2016, 11, 5633-5643, incorporated herein by reference in its entirety) studied the effect of nano-$ZrO_2$ on a repaired denture base, and discovered a significant increase in its transverse strength, especially with high nano-$ZrO_2$ concentrations. Despite these improvements in mechanical performance, a method for inhibiting *C. albicans* adhesion and colonization to dental appliances is still needed.

In view of the forgoing, one objective of the present invention is to provide a method of preventing or treating an oral infection in a subject by having the subject wear an acrylic dental appliance repaired using an autopolymerizing acrylic reinforcement resin comprising zirconium dioxide nanoparticles. Another objective of the present invention is to provide a method of preventing or reducing adhesion of a microorganism to a dental appliance fabricated by, coated with, or containing an autopolymerizing acrylic reinforcement resin comprising zirconium dioxide nanoparticles.

BRIEF SUMMARY OF THE INVENTION

According to a first aspect, the present invention relates to a method of preventing or treating an oral infection in a subject by preventing or reducing adhesion of a microorganism to a repaired acrylic dental appliance worn by the subject. The method includes (i) dispersing a nanocomposite powder having (a) an acrylic polymer powder including polymethyl methacrylate, and (b) zirconium dioxide nanoparticles in a monomer liquid having methyl methacrylate thereby forming a reinforcement resin, (ii) applying and packing the reinforcement resin in excess to a repair gap of an acrylic dental appliance, and (iii) autopolymerizing the reinforcement resin thereby forming the repaired acrylic dental appliance.

In one embodiment, the microorganism is selected from the group consisting of bacteria and fungi.

In one embodiment, the microorganism is a fungus selected from the *Candida* species.

In one embodiment, the nanocomposite powder includes 1-10 wt % zirconium dioxide nanoparticles relative to a total weight of the nanocomposite powder.

In one embodiment, the zirconium dioxide nanoparticles have an average size of 20-110 nm, and an average surface area of 5-15 $m^2/g$.

In one embodiment, the reinforcement resin has a nanocomposite powder to monomer liquid mass ratio in a range of 0.5:1 to 3:1.

In one embodiment, the autopolymerizing is performed at a temperature of 20-50° C., and a pressure of 10-50 psi.

In one embodiment, the method further includes treating the zirconium dioxide nanoparticles with a silane coupling reagent prior to the dispersing.

In one embodiment, preventing or reducing adhesion of a microorganism to the repaired acrylic dental appliance is evaluated by measuring a microbial count.

In one embodiment, the acrylic dental appliance is a denture.

In one embodiment, the oral infection is denture stomatitis.

According to a second aspect, the present invention relates to a method of preventing or reducing adhesion of a microorganism to a dental appliance. The method includes (i) dispersing a nanocomposite powder having (a) an acrylic polymer powder including polymethyl methacrylate, and (b) zirconium dioxide nanoparticles in a monomer liquid comprising methyl methacrylate thereby forming a reinforcement resin, (ii) applying and packing the reinforcement resin directly into a mold of the dental appliance, and (iii) autopolymerizing the reinforcement resin thereby forming the dental appliance.

In one embodiment, the microorganism is selected from the group consisting of bacteria and fungi.

In one embodiment, the microorganism is a fungus selected from the *Candida* species.

In one embodiment, the nanocomposite powder includes 1-10 wt % zirconium dioxide nanoparticles relative to a total weight of the nanocomposite powder.

In one embodiment, the zirconium dioxide nanoparticles have an average size of 20-110 nm, and an average surface area of 5-15 $m^2/g$.

In one embodiment, the reinforcement resin has a nanocomposite powder to monomer liquid mass ratio in a range of 0.5:1 to 3:1.

In one embodiment, the autopolymerizing is performed at a temperature of 20-50° C., and a pressure of 10-50 psi.

In one embodiment, the method further includes treating the zirconium dioxide nanoparticles with a silane coupling reagent prior to the dispersing.

In one embodiment, preventing or reducing adhesion of a microorganism to the dental appliance is evaluated by measuring a microbial count.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
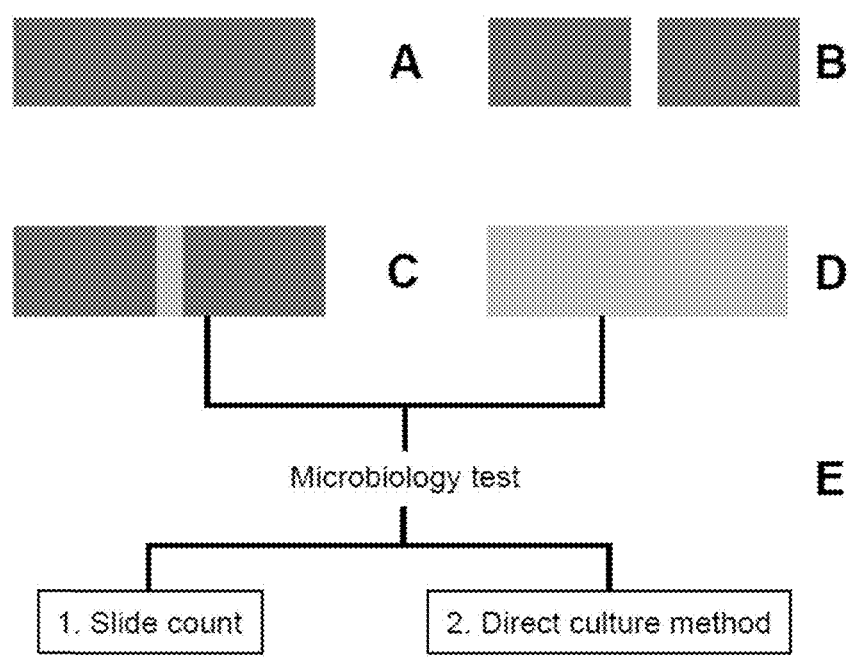
FIG. 1 is a graph illustrating the workflow of specimens' preparation, in which (A) represents intact heat polymerized specimens, (B) represents sectioned heat polymerized specimens, (C) represents repaired heat polymerized specimens exemplifying repaired denture base (n=60), (D) represents intact cold-cured acrylic resin specimens exemplifying interim removable prostheses (n=60), and (E) represents exposed (C) and (D) for microbiology tests.

Embodiments of the present disclosure will now be described more fully hereinafter with reference to the accompanying drawings, in which some, but not all embodiments of the disclosure are shown.

Unless otherwise specified, "a" or "an" means "one or more". Additionally, within the description of this disclosure, where a numerical limit or range is stated, the endpoints are included unless stated otherwise. Also, all values and subranges within a numerical limit or range are specifically included as if explicitly written out.

As used herein, "reinforcement resin" refers to a material formed by dispersing a nanocomposite powder having (a) an acrylic polymer powder including polymethyl methacrylate, and (b) zirconium dioxide nanoparticles in a monomer liquid comprising, consisting essentially of, or consisting of methyl methacrylate.

As used herein, "acrylic polymer" or "acrylic resin" refers to a group of related thermoplastic or thermosetting plastic substances derived from acrylate, methacrylate, acrylic acid, methacrylic acid or other related compounds. As used herein polymethyl methacrylate or poly(methyl methacrylate) or PMMA, also known as acrylic or acrylic glass as well as by the trade names Plexiglas, Acrylite, Lucite, and Perspex among several others refers to a typically transparent thermoplastic.

As used herein, the monomer liquid may include monomers and prepolymers having one or more polymerizable groups such as acryl, methacryl, vinyl and the like. The monomer liquid may further include a polymerization initiator. Additional components may also be included, such as a polymerization accelerator, a polymerization stabilizer and the like.

As used herein, monomers and prepolymers may include a mono-functional or multifunctional acrylate or methacrylate derivative, more preferably a methacrylate derivative. Specifically, mono-functional monomers useful in the present invention include, but are not limited to, methyl methacrylate (MMA), isopropyl methacrylate, n-propyl methacrylate, isopropyl methacrylate, n-butyl methacrylate, isobutyl methacrylate, hydroxyethyl methacrylate, hydroxypropyl methacrylate, hydroxybutyl methacrylate, propylene glycol monomethacrylate, poly(ethylene glycol) monomethacrylate, isobornyl methacrylate, methoxyethoxyethyl methacrylate, ethoxyethoxyethyl methacrylate, tetrahydrofurfuryl methacrylate, acetoxyethyl methacrylate, phenoxyethylmethacrylate, and mixtures thereof. Useful multifunctional monomers and prepolymers include, but are not limited to, ethyleneglycol dimethacrylate, diethyleneglycol dimethacrylate, trimethyleneglycol dimethacrylate, triethyleneglycol dimethacrylate, trimethylolpropane trimethacrylate, tetraethyleneglycol dimethacrylate, 1,3-propanediol dimethacrylate, 1,4-butanediol dimethacrylate, 1,6-hexanediol dimethacrylate, 1,12-dodecanediol dimethacrylate, polyethyleneglycol dimethacrylate, trimethylolpropane trimethacrylate, 1,2,4-butanetriol trimethacrylate, pentaerythritol tetramethacrylate, bisphenol A-glycidyl methacrylate (Bis-GMA), ethoxylated bisphenol A-dimethacrylate (EBPADMA), urethane dimethacrylate (UDMA), diurethane dimethacrylate (DUDMA), polyurethane dimethacrylate (PUDMA), polycarbonate dimethacrylate (PCDMAL), and mixtures thereof.

Further exemplary methacrylate derivatives suitable for the purpose of the invention are those formed by the reaction of methacrylic acid with a monofunctional glycidyl ethers (epoxies) such as butyl glycidyl ether, cresyl glycidyl ether, phenyl glycidyl ether, and other epoxies such as limonene oxide. Also preferred are carbamate (urethane) adducts of hydroxyethylmethacrylate or hydroxyethylmethacrylate or hydroxypropylmethacrylate with mono functional isocyanates including, but not limited to, methylisocyanate, ethylisocyanate, propylisocyanate, isopropylisocyanate, butylisocyanate, isobutylisocyanate, phenylisocyanate, or an adduct of isocyanatoethylmethacrylate with an hydroxyl compound such as methanol, ethanol and the like.

According to a first aspect, the present invention relates to a method of preventing or treating an oral infection in a subject by preventing or reducing adhesion of a microorganism to a repaired acrylic dental appliance worn by the subject. The method includes (i) dispersing the nanocomposite powder having (a) the acrylic polymer powder including polymethyl methacrylate, and (b) zirconium dioxide nanoparticles in the monomer liquid having methyl methacrylate thereby forming the reinforcement resin, (ii) applying and packing the reinforcement resin in excess to a repair gap of an acrylic dental appliance, and (iii) autopolymerizing the reinforcement resin thereby forming the repaired acrylic dental appliance. A detailed description on repairing methods is disclosed in patent application titled "A Method of Repairing an Acrylic Denture Base and Zirconia Autopolymerizable Resins Thereof" (Application No. 62/503,706—incorporated herein by reference).

In most embodiments, an excessive amount of the reinforcement resin is applied and packed to a repair gap of an acrylic dental appliance to compensate for volume shrinkage during a polymerization process. Specifically, the amount of the reinforcement resin applied and packed to a repair gap may be in the range of 105-150 wt %, preferably 110-135 wt %, more preferably 120-130 wt % relative to the total amount of reinforcement resin needed to fill the overall repair gap of an acrylic dental appliance.

In a preferred embodiment, autopolymerization of the reinforcement resin proceeds by a self-curing process without assistance from any extra polymerization initiators. In some embodiments, a polymerization initiator is included in the monomer liquid at a concentration in a range of about 0.01% to about 5.0% by weight. Exemplary polymerization initiators include, but are not limited to, benzoyl peroxide, lauroyl peroxide, methyl ethyl ketone peroxide (MEKP), camphorquinone (CQ), benzil, benzophenone, azobisisobutyronitrile (AIBN), and phenylbis(2,4,6-trimethylbenzoyl) phosphine oxide (Irgacure 819, BASF).

In some embodiments, a polymerization accelerator that works in conjunction with the polymerization imitator to promote or improve the speed of polymerization reaction is added to the monomer liquid at a concentration in a range of about 0.01% to about 5.0% by weight. Exemplary polymerization accelerators include, but are not limited to, N,N-dimethyl-p-toluidine, N,N-bis(2-hydroxyethyl)-p-toluidine, ethyl 4-(dimethylamino)benzoate, dimethylaminoethyl methacrylate, and N-(2-cyanoethyl)-N-methyl aniline.

In order to achieve a normal level of storage stability, especially for compositions that are cured through a free-radical curing mechanism, it may be desirable to include a polymerization inhibitor to the monomer liquid at a concentration of up to about 1.0% by weight. Examples of polymerization inhibitors include hydroquinone, 4-methoxyphenol, 2,6-di-tert-butyl-4-methylphenol (BHT) and the like.

As used herein, zirconium dioxide ($ZrO_2$), also known as zirconia, is a white crystalline oxide of zirconium. Its most naturally occurring form, with a monoclinic crystalline structure, is the mineral baddeleyite. Zirconia may be produced by calcining zirconium compounds, exploiting its high thermal stability. Three phases are known: monoclinic (~<1170° C.), tetragonal (~1170-2370° C.), and cubic (~>2370° C.). The trend is for higher symmetry at higher temperatures, as is usually the case. In certain embodiments, a few percentages of the oxides of calcium or yttrium stabilize the cubic phase. The rare mineral tazheranite (Zr, Ti, Ca)$O_2$ is cubic. Unlike $TiO_2$, which features six-coordinate Ti in all phases, monoclinic zirconia consists of seven-coordinate zirconium centers. This difference may be attributed to the larger size of the Zr atom relative to the Ti atom.

Zirconium dioxide is one of the most studied ceramic materials. $ZrO_2$ adopts a monoclinic crystal structure at room temperature and transitions to tetragonal and cubic at higher temperatures. The change of volume caused by transitions induces large stresses, which may cause it to crack upon cooling from high temperatures. When zirconia is blended with other oxides, the tetragonal and/or cubic phases may be stabilized. Exemplary effective dopants include, but are not limited to, magnesium oxide (MgO), yttrium oxide ($Y_2O_3$, yttria), calcium oxide (CaO), and cerium (III) oxide ($Ce_2O_3$).

In a preferred embodiment, the nanocomposite powder includes 1-10 wt % zirconium dioxide nanoparticles relative to the total weight of the nanocomposite powder, preferably 1.5-9.5 wt %, preferably 2.5-9.0 wt %, preferably 3.5-8.5 wt %, preferably 4.5-8.0 wt %, preferably 5.5-7.5 wt % zirconium dioxide nanoparticles relative to the total weight of the nanocomposite powder.

In a preferred embodiment, the zirconium dioxide nanoparticles are substantially granular or substantially spherical (e.g. oval or oblong in shape). In certain embodiments, the zirconium dioxide nanoparticles may be of any shape that provides suitable reinforcement to the repaired acrylic denture base. In certain embodiments, the nanoparticles may be in the form of at least one shape selected from the group including, but not limited to, a sphere, a rod, a cylinder, a 3-dimensional form having one or more sides in the form of a rectangle, a triangle, a pentagon, and/or a hexagon, a prism, a disk, a platelet, a fiber, a cube, a cuboid, and tube, and an urchin (e.g. a globular particle possessing a spiky uneven surface).

In a preferred embodiment, the nanoparticles of the present disclosure may be uniform. As used herein, the term "uniform" refers to no more than 10%, preferably no more than 5%, preferably no more than 4%, preferably no more than 3%, preferably no more than 2%, preferably no more than 1% of the distribution of the nanoparticles having a different shape. For example, nanoparticles are uniform and have no more than 1% of nanoparticles in an oblong shape. In certain embodiments, the nanoparticles may be non-uniform. As used herein, the term "non-uniform" refers to more than 10% of the distribution of the nanoparticles having a different shape.

As used herein, a particle size refers to the longest linear distance measured from one point on the particle though the center of the particle to a point directly across from it. In a preferred embodiment, the zirconium dioxide nanoparticles of the present disclosure in any of their embodiments have an average granularity and/or average particle size of 10-110 nm, preferably, 15-90 nm, preferably 20-80 nm, preferably 25-70 nm, preferably 30-60 nm, preferably 32-50 nm, preferably 34-46 nm, preferably 36-44 nm, preferably 38-42 nm.

The Brunauer-Emmet-Teller (BET) theory (S. Brunauer, P. H. Emmett, E. Teller, *J. Am. Chem. Soc.* 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. In most embodiments, BET surface area is measured by gas adsorption analysis, preferably $N_2$ adsorption analysis. In a preferred embodiment, the zirconium dioxide nanoparticles of the present disclosure in any of their embodiments have an average BET surface area of 5-15 $m^2/g$, preferably 5.5-14 $m^2/g$, preferably 6-13 $m^2/g$, preferably 6.5-12 $m^2/g$, preferably 7-11 $m^2/g$, preferably 7.5-10.5 $m^2/g$, preferably 8-10 $m^2/g$, preferably 8.5-9.5 $m^2/g$.

In a preferred embodiment, zirconium dioxide nanoparticles are premixed with the acrylic polymer powder to form a powder mixture before dispersing. In one embodiment, the mixture is mixed using a mortar and pestle, or a spatula. In one embodiment, the mixture is mixed using a centrifugal mixer with a rotational speed of at least 250 rpm, preferably at least 500 rpm, more preferably at least 1000 rpm. In one embodiment, the mixture is mixed by a powder mixer.

In a preferred embodiment, autopolymerization of the reinforcement resin is carried out by a self-curing or autopolymerizing process which starts spontaneously when the monomer liquid compound and the nanocomposite powder are brought into contact, for example, by mixing. In a preferred embodiment, the polymerizing is performed at a temperature of 20-50° C., preferably 20-45° C., more preferably 20-40° C., more preferably 20-35° C., most preferably 20-30° C., preferably 22-28° C., preferably 24-26° C. and a pressure of 10-50 psi, preferably 11-40 psi, preferably 12-30 psi, preferably 13-25 psi, preferably 14-20 psi, preferably 14.5-18 psi. According to these embodiments, these components of the self-curing or autopolymerizing systems are preferably contained in at least two separate containers or compartments. In certain embodiments, when a polymerization initiator is included, the reinforcement resin may be polymerized at a different temperature compared to autopolymerization temperatures, e.g. 55-200° C., 75-150° C., or 90-125° C., or be photopolymerized using an external light source, e.g. an ultraviolet and/or a visible light.

In a preferred embodiment, the reinforcement resin has a nanocomposite powder to monomer liquid mass ratio in a range of 0.5:1 to 3:1, preferably 1:1 to 2.5:1, preferably 1.5:1 to 2.33:1, preferably 1.75:1 to 2.25:1, preferably 1.8:1 to 2.2:1, preferably 1.9:1 to 2.1:1, or about 2:1.

In most embodiments, the method further comprises treating the zirconium dioxide nanoparticles with a silane coupling reagent prior to the dispersing. In a preferred embodiment, the silane coating covers only a portion of a total surface of the zirconium dioxide nanoparticles. Specifically, the silane coating may cover up to 50%, up to 60%, up to 75%, or up to 90% of a total surface area of the zirconium dioxide nanoparticles. Typical silane derivatives (herein also termed "silanes") suitable for the purpose of the invention include, but are not limited to, silanes bearing a methacrylic functional group such as methacryloxypropyl trimethoxy silane; silanes bearing an epoxy group such as glycidoxy propyl trimethoxy silane or beta-(3,4-epoxycyclohexyl)ethyl trimethoxysilane; silanes comprising an amino functional group such as gamaaminopropyl trimethoxy silane, gama-aminopropyl triethoxy silane or N-beta(aminoethyl)gama-aminopropyl trimethoxy silane); silanes comprising a mercapto group such as 3-mercaptopropyl trimethoxy silane; or a mixture thereof, or a mixture of one or more of the above silanes with an alkyl or aryl silane, where the alkyl or aryl group contains no reactive functional groups to connect to the organic polymer, such as phenyl trimethoxy silane and other phenyl silanes. Addition of an alkyl or aryl silane improves adhesion and adds hydrophobicity. The use of the hydrophobic silanes is beneficial for preventing moisture penetration into the reinforcement resin. The zirconium nanoparticles are preferably pre-treated with the silane derivative or, alternatively, a small amount of a silane derivative may be added to the nanocomposite powder, the monomer liquid, and/or the reinforcement resin. In a preferred embodiment, the silane coupling reagent is 3-(trimethoxysilyl)propyl methacrylate. In some embodiments, the amount of the silane coating is in the range of 1-20 wt %, preferably 2.5-15 wt %, more preferably 5-10 wt % relative to the total weight of the nanocomposite powder. It is equally envisaged that titante derivatives may be used in addition to and/or in lieu of the silane coupling reagent.

In a preferred embodiment, the treating comprises immersing the zirconium dioxide nanoparticles in a solution comprising 1.0-5.0 g of the silane coupling reagent per liter of the solution, preferably 1.5-4.5 g, preferably 2.0-4.0 g, preferably 2.5-3.5 g, preferably 2.75-3.25 g, or about 3.0 g of the silane coupling reagent per liter of the solution. The solution preferably comprises a solvent. As used herein, the term "solvent" refers to a non-polar, polar aprotic, or polar-protic solvent and includes, but is not limited to, ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, mixtures of xylenes, toluene, mesitylene, anisole, 1,2-dimethoxybenzene, α,α,α-trifluoromethylbenzene, fluorobenzene), chlorinated solvents (e.g. chlorobenzene, dichloromethane, 1,2-dichloroethane, 1,1-dichloroethane, chloroform), amide solvents (e.g. dimethylformamide, dimethylacetamide, N-methyl-2-pyrrolidone), ketones (e.g. acetone, butanone), hexane, dimethyl sulfoxide, acetonitrile, propionitrile, butyronitrile, benzonitrile, and mixtures thereof.

In certain embodiments, the reinforcement resin may further include a pigment, primarily for aesthetic reasons. Any organic and inorganic pigment is suitable for the purpose of the invention, provided it is not toxic as are some cadmium and lead compounds. Suitable pigments and dyes include, but are not limited to, titanium dioxide, zinc oxide, lake pigments and the like. The pigment is preferably pre-grinded into one of the components of the system, since it is unlikely to function well if added as a separate powder. The pigment may present in 0.01-1 wt % relative to the total weight of the reinforcement resin, preferably 0.1-0.8 wt %, preferably 0.2-0.6 wt %, preferably 0.3-0.5 wt % relative to the total weight of the reinforcement resin.

The surface roughness of dental appliances may play a role in microorganism adhesion and accumulation, with lower surface roughness values (smoother surface) helping to prevent adhesion. The surface roughness can be determined by atomic force microscopy (AFM), scanning electron microscopy (SEM), transmission electron microscopy (TEM), an optical profiler, and/or a rugosimeter. In some embodiments, the reinforcement resin has a surface roughness characterized by a profile roughness parameter Ra (arithmetical mean deviation of the assessed surface profile) of 0.01-10 um, preferably 0.05-5 um, 0.1-2.5 um, preferably 0.2-2.0 um, preferably 0.25-1.0 um. In at least one embodiment, the reinforcement resin has a smoother surface (a lower surface roughness) compared to a control resin, e.g. a resin prepared by a material without reinforcement zirconium dioxide nanoparticles.

The reinforcement resin of the current disclosure may further include a fluoride source selected from sodium fluoride, potassium fluoride, aluminum fluoride, zinc fluoride, stannous fluoride, ammonium fluoride, sodium monofluorophosphate and the like. The fluoride source may present in an amount of 0.01-2 wt % relative to the total weight of the reinforcement resin.

In addition to zirconium dioxide nanoparticles, the reinforcement resin may further include a conventional antimicrobial agent, e.g. triclosan, chlorhexidine, cetyl pyridinium chloride, benzethonium chloride, bromochlorophene, and quaternary ammonium salts such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, undecylenic acid, fluconazole, amphotericin B, sphingosine, and nystatin. The conventional antimicrobial agent may be included in an amount of 0.1-5 wt % relative to the total weight of the reinforcement resin.

As used herein, "microorganism" or "microbe" refers to in particular fungi, and gram-positive and gram-negative bacteria.

In some embodiments, preventing or reducing adhesion of a microorganism to the repaired acrylic dental appliance is evaluated by measuring a microbial count. Preferably, the number of viable microorganisms adhering to the repaired acrylic dental appliance is counted using a slide count method and/or a direct culture method (plate count).

The "slide count" method utilizes a microscope slide in a chamber that is especially designed to enable cell counting. A total number of cells in a sample can be determined by looking at the sample under a microscope and counting the number manually. A number of viable cells can also be determined using the slide count method if a viability dye is added to the sample. Exemplary viability dyes include, but are not limited to, Trypan Blue, Calcein-AM, Erythrosine B, propidium iodide, and 7-aminoactinomycin D.

"Colony-forming unit (CFU)" refers to a unit used to estimate the number of viable bacteria or fungal cells in a sample. The purpose of direct culture method (plate count) is to estimate the number of cells present based on their ability to give rise to colonies under specific conditions of nutrient medium, temperature and time. Theoretically, one viable cell can give rise to a colony through replication. A sample solution of microbes at an unknown concentration is often serially diluted in order to obtain at least one plate with a countable number of CFUs. Counting colonies is performed manually using a pen and a click-counter, or automatically using an automated system and a software tool for counting CFUs.

In other embodiments, the number of viable microorganisms adhering to the repaired acrylic dental appliance is determined by automated cell counting methods using a Coulter counter, a flow cytometry, an image analysis, and/or indirect cell counting methods using a spectrophotometer.

Preventing or reducing adhesion may be understood to indicate a reduction of the number of adhering microorganism cells. In some embodiments, the adhesion of microorganisms to the acrylic dental appliance repaired by the reinforcement resin characterized by a microbial count is reduced by at least 10%, preferably at least 20%, more preferably at least 30%, more preferably at least 40%, more preferably at least 45%, more preferably at least 50%, more preferably at least 55%, more preferably at least 60%, more preferably at least 65%, more preferably at least 70%, more preferably at least 80%, more preferably at least 90%, or more preferably at least 95%, with respect to an untreated control acrylic dental appliance, e.g. an acrylic dental appliance repaired by a material without reinforcement zirconium dioxide nanoparticles. Ideally, the adhesion of microorganisms to the repaired acrylic dental appliance may be completely or almost completely prevented.

In some embodiments, the adhesion of pathogenic species of fungi to the repaired acrylic dental appliance is prevented or reduced. Exemplary pathogenic fungi include classes of ascomnycota, basidomnycota, deuteromycota and zygomycota, particularly human pathogenic forms of *candida*, which is one of the most common causes of fungal infections worldwide. *Candida* species populate skin and mucous membranes even for healthy persons. Overgrowth of pathogenic forms of *candida* can cause fungal infection candidiasis ranging from superficial, such as thrush (oropharyngeal candidiasis) and vulvovaginal candidiasis, to systemic, such as fungemia and invasive candidiasis.

In a preferred embodiment, the adhesion of *candida* species to the repaired acrylic dental appliance is prevented or reduced. Exemplary pathogenic *candida* (abbreviated to *C.* in the following) species include, but are not limited to *C. albicans, C. auris, C. glabrata, C. tropicalis, C. parapsilosis, C. krusei, C. guiliermondii, C. lusitaniae, C. kefyr, C. famata, C. inconspicua, C. rugosa, C. dubliniensis, C parapsilosis, C. norvgensis, C. orthoparapsilosis, C. stellatoidea, C. boidinii, C. catenulate, C. ciferii, C. haemulonii, C. lipolytica, C. pulcherrnima, C. utilis,* and *C. viswanathii.* Other notable *candida* species include *C. aaseri, C. actiscondensi, C. acutus, C. agrestis, C. agresis, C. amapae, C. anatomiae, C. ancudensis, C. antarctica, C. antillancae, C. apicola, C. apis, C. aquaetextoris, C. aquatica, C. atlantica, C. atmosphaerica, C. auringiensis, C. azyma, C. beechii, C. benhamii, C. bertae, C. berthetii, C. blakii, C. boleticola, C. bombi, C. boarzewiae, C brumptii, C. buffonii, C. buinensis, C cacaoi, C. cantarellii, C. capsuligena, C. cariosilignicola, C. caseinolytica, C. castellii, C. chalmersi, C. chilensis, C. chiropterorum, C. claussenii, C. coipomensis, C. colliculosa, C. conglobata, C. curiosa, C. cylindracea, C. dendrica, C. dendronema, C. deserticola, C. diddensiae, C. diffluens, C. diversa, C. drymisii, C. edax, C. entomophila, C. eremophila, C. ergatensis, C. ernobii, C. etchellsii, C. etchellsii, C. ethanolica, C. ethanothermophilumn, C. evantina, C. fabiani, C. fennica, C. flareri, C. fluviotilis, C. fragariorum, C. fragi, C. fragicola, C. freyschussi, C. friledrichii, C. fructus, C. fusiformata, C. geochares, C. glaebosa, C. graminis, C. gropengiesseri, C. hellenica, C. heveanensis, C. holmii, C. homnilentoma, C. humicola, C. humilis, C. iberica, C. incommunis, C. ingens, C. insectalens, C. insectamans, C. insectorusme, C. intermedia, C. ishiwadae, C. japonica, C. javanica, C. kara-waiewii, C. kruisii, C. krusoides, C. lactiscondensi, C. lambica, C. laureliae, C. llanquihuensis, C. lodderae, C. lusitaniae, C. magnoliae, C. malicola, C. maltosa, C. maris, C. maritima, C. melibiosica, C. melinii, C. membranaefaciens, C. mesenterica, C. methanosorbosa, C. milleri, C. mogii, C. molischiana, C. monosa, C. montana, C. mucilaginosa, C. muitis-gemmis, C. musae, C. muscorum, C. mycoderma, C. naeodendra, C. nakasei, C. nemodendra, C. nitratophila, C. novakii, C. oleophila, C. oregonensis, C panyrana, C, padigen, C. paludigena, C. pararugosa, C. peliculosa, C. petata, C. periphelosum, C. petrohuensis, C. pignaliae, C. pintolopesii, C. pinus, C. piacentae, C. polymorpha, C. populi, C. pseudotropicalis, C. psychrophila, C. punzica, C. quercitrusa, C. quercuum, C. railenensis, C. ralunensis, C. reukaujfi, C. rhagii, C, rugopeliculosa, C. saitoana, C. sake. C salmanticensis, C. santamariae, C. santjacobensis, C. savonica, C. schatavii, C. sequanensis, C. shehatae, C. silvae, C. silvanorum, C. silvicultrix, C. solani, C. sonorensis, C. sophiae-reginae, C. sorboxylosa, C. spandovensis, C. sphaerica, C. stellata, C. succiphila, C sydowiorum, C. anzawaensis, C. tenuis, C. tepae, C. terebra, C. torresii, C. tsuchiyae, C tsukubaensis, C. valdiviana, C. valida, C. vanderwaltii, C. vartiovaarai, C. versatilis, C. vini, C. wickerhamnii, C. xestobii,* and *C. zeylanoides.*

As used herein, exemplary dental appliances include, but are not limited to, denture bases, removable partial dentures, complete dentures, temporary crowns and bridges, orthodontic functional appliances including retainers, mouth guards, implant-supported fixed interim prostheses and the like.

Oral candidiasis (oral thrush) is candidiasis that occurs in the mouth. *C. albicans* is the most commonly implicated organism in oral candidiasis such as denture stomatitis (also termed as denture-related stomatitis or *candida*-associated denture induced stomatitis). Denture stomatitis is a common fungal infection where mild inflammation and redness of an oral mucous membrane occur upon contacting with a dental appliance such as a denture, a removable prosthesis, or an orthodontic functional appliance. *Candida* species are the major contributor to denture stomatitis, while *C. albicans* is the most commonly isolated microorganism from a surface of a dental appliance worn by a subject. *C. albicans* cells often form biofilms on solid surfaces, with characteristic three-dimensional structures that display a high level of antifungal resistance. After initially adhering to the surface, *C. albicans* biofilms grow on the surface and subsequently produce invasive filaments that penetrate neighboring cells. In at least one embodiment, the repaired acrylic dental appliance of the current invention is employed for the prevention and treatment of denture stomatitis in a subject by reducing or preventing adhesion of *C. albicans* to a surface of the repaired acrylic dental appliance.

In some embodiments, the adhesion of pathogenic gram-positive bacteria to the repaired acrylic dental appliance is prevented or reduced. Notable oral bacteria include, but are not limited to *Propionibacterium acnes, Stapylococcus aureus, Streptococcus pyogenes, Corynebacteriurn tenuis, Corynebacterium diphtheriae, Corynebacterium minutissimum, Micrococcus sedentarius, Bacillus anthracis, Neisseria meningitides, Neisseria gonorrhoeae, Pseudomonas aeruginosa, Pseudomonas pseudonmallei, Borrelia burgdoiferi, Treponeina pallidurm, Mycobacteriumn tuberculosis, Escherichia coli, Streptococcus gorcdonii, Streptococcus mnutans, Streptococcus salivarius, Actinormyces naesuhmdii, Salmonella species, Nitrosomonas species, Aquabacterium species, Stenotrophomnonas species, Xanthomonas species, Haemophilus species,* as well as all microorganisms that are described by Paster et al. (Paster B J, Boches S K, Galvin J L, Ericson R E, Lau C N, Levanos V A, Sahasrabudhe A, Dewhirst F E. Bacterial diversity in human subgingival plaque. *J. Bacteriol.* 2001, 12, 3770-3783, incorporated herein by reference in its entirety).

Pathogenic oral bacteria such as *Streptococcus mutans*, *Streptococcus sanguinis* and *Streptococcus salivarius* are associated with oral diseases including tooth decay, oral cavity, periodontal diseases, gingivitis, pericoronitis, and endodontitis.

According to a second aspect, the present invention relates to a method of preventing or reducing adhesion of a microorganism to a dental appliance. The method includes (i) dispersing the nanocomposite powder having (a) the acrylic polymer powder including polymethyl methacrylate, and (b) zirconium dioxide nanoparticles in the monomer liquid comprising methyl methacrylate thereby forming the reinforcement resin, (ii) applying and packing the reinforcement resin directly into a mold of the dental appliance, and (iii) autopolymnerizing the reinforcement resin thereby forming the dental appliance.

In some embodiments, the method of preventing or reducing adhesion of a microorganism to a dental appliance further relates to (i) coating at least a portion of a surface of the dental appliance with the reinforcement resin, and (ii) autopolymerizing the reinforcement resin thereby forming a dental appliance with a reinforcement resin coating, wherein the coating comprises a number of layers, and wherein the concentration of zirconium dioxide nanoparticles is different in at least two coating layers. In a preferred embodiment, the coating has a concentration gradient of zirconium dioxide nanoparticles in the coating, with the coating having a higher zirconium dioxide nanoparticles concentration at an outer coating layer and the coating having a lower zirconium dioxide nanoparticles concentration at an inner layer. The concentration gradient of zirconium dioxide nanoparticle in the coating may be achieved by applying layers of reinforcement resin with increasing concentration of zirconium dioxide. The layer with the lowest concentration of zirconium dioxide is first applied to a surface of the dental appliance followed by autopolymerizing, with successive layers of increasing zirconium dioxide concentration applied atop one another. Specifically, the zirconium dioxide nanoparticle concentration at an outermost surface of the reinforcement resin coating may be in the range of about 5 wt % to about 10 wt %, about 6 wt % to about 9 wt %, about 7 wt % to about 8 wt %, or approximately about 7.5 wt % relative to a total weight of the nanocomposite powder, and wherein the zirconium dioxide nanoparticle concentration at an innermost surface is in the range of about 0.5 wt % to about 4.5 wt %, about 1 wt % to about 4 wt %, about 2 wt % to about 3 wt %, or approximately about 2.5 wt % relative to a total weight of the nanocomposite powder.

In some embodiments, the reinforcement resin coating covers at least 20%, at least 40%, preferably at least 50%, more preferably at least 60%, more preferably at least 70%, more preferably at least 80%, or more preferably at least 90% of a total surface area of the dental appliance.

Preventing or reducing adhesion may be understood to indicate a reduction of the number of adhering microorganism cells. In some embodiments, the adhesion of microorganisms to the dental appliance fabricated by, coated with, and/or containing the reinforcement resin characterized by a microbial count is reduced by at least 10%, preferably at least 20%, more preferably at least 30%, more preferably at least 40%, more preferably at least 45%, more preferably at least 50%, more preferably at least 55%, more preferably at least 60%, more preferably at least 65%, more preferably at least 70%, more preferably at least 80%, more preferably at least 90%, or more preferably at least 95%, with respect to a control untreated dental appliance, e.g. a dental appliance fabricated by, coated with, and/or containing a material without reinforcement zirconium dioxide nanoparticles. Ideally, the adhesion of microorganisms to the dental appliance may be completely or almost completely prevented.

In at least one embodiment, the dental appliance of the current invention is employed for the prevention and treatment of denture stomatitis in a subject by reducing or preventing adhesion of *C. albicans* to a surface of the dental appliance.

Having generally described this disclosure, a further understanding can be obtained by reference to certain specific examples which are provided herein for purposes of illustration only and are not intended to be limiting unless otherwise specified. The examples below are intended to further illustrate protocols for repairing acrylic denture bases and fabricating removable interim dentures and orthodontic appliances employing an autopolymerizable acrylic reinforcement resin comprising zirconium dioxide nanoparticles of the current invention. Further, they are intended to illustrate evaluating the inhibitory effect of these materials on *Candida albicans* adhesion to repaired acrylic denture bases and removable interim dentures and orthodontic appliances. They are not intended to limit the scope of the claims.

Example 1

Materials and Methods

The study was conducted using cold-cured acrylic resin as a repair material (repair group), which could affect the mechanical behavior of denture repair and its ability to provide antifungal activity, while the other intact cold-cured group was used for removable prosthesis fabrication. Therefore, from a clinical perspective, the results of the current study supported that nano-$ZrO_2$-reinforced cold-cured acrylic resin could be used as a valuable treatment protocol in two ways: as a repair material and as a material used in the fabrication of removable interim dentures and orthodontic appliances.

i. Preparation of Heat-Polymerized Specimens

A total of 60 rectangular acrylic resin specimens were made using a metal mold with dimensions of 22×10×2.5 $mm^3$ (FIG. 1). Specimens' wax-up (Cavex Set Up Wax; Cavex, Haarlem, the Netherlands) procedures were performed within the mold and invested using a dental stone (Fujirock E P; G C, Leuven, Belgium) within a flask (61B Two Flask Compress; Handler Manufacturing, Westfield, N.J., USA). The wax was burned out after the complete set of the dental stone. Powder and monomer of heat-polymerized acrylic resin (Major.Base.20, Major Prodotti Dentari SPA, Moncalieri, Italy) were mixed following the manufacturer's instructions and packed in the dough stage into the mold cavity. The flask closure was completed and kept under pressure for 30 min. Acrylic resin specimens were processed for 8 hours in a water bath at 74° C. followed by 1 hour processing at 100° C. using a thermal curing unit (KaVo Elektrotechnisches Werk GmbH, Leutkirch, Germany). After polymerization, specimens within flasks were bench cooled prior to deflasking. According to manufacturer's recommendations, finishing and polishing procedures were performed using a tungsten carbide bur (HM251FX-040-HP; Meisinger, Centennial, Colo., USA) and acrylic polisher (HM251FX-060; Meisinger) for all specimens' surfaces except for the intaglio surface (tissue-side surface). The intact heat-polymerized acrylic resin specimens were assigned randomly to four groups with 15 repaired specimens each (Table 1).

TABLE 1

Grouping and coding of the specimens according to ZrO$_2$ nanoparticles concentrations

| Group | Code | Description | No. |
|---|---|---|---|
| R, repair | RAP | Specimens repaired with pure autopolymerized resin | 15 |
| | 2RN | Specimens repaired with autopolymerized resin reinforced with 2.5% w.t. nano-ZrO$_2$ | 15 |
| | 5RN | Specimens repaired with autopolymerized resin reinforced with 5% w.t. nano-ZrO$_2$ | 15 |
| | 7RN | Specimens repaired with autopolymerized resin reinforced with 7.5% w.t. nano-ZrO$_2$ | 15 |
| I, intact | AP | Intact pure autopolymerized resin | 15 |
| | 2AP | Intact autopolymerized specimen resin reinforced with 2.5% w.t. nano-ZrO$_2$ | 15 |
| | 5AP | Intact autopolymerized specimen resin reinforced with 5% w.t. nano-ZrO$_2$ | 15 |
| | 7AP | Intact autopolymerized specimen resin reinforced with 7.5% w.t. nano-ZrO$_2$ | 15 |

Abbreviation:
nano-ZrO$_2$, zirconium dioxide nanoparticles.

ii. Repair Material Preparation

Figure 2A:
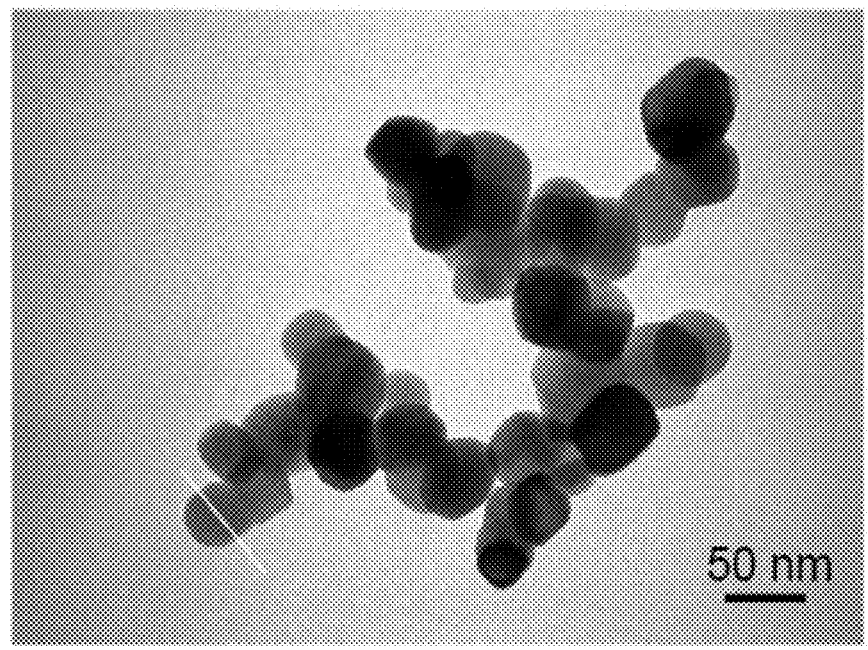
FIG. 2A is a transmission electron microscopy (TEM) image of several $ZrO_2$ nanoparticles. The scale bar corresponds to 50 mm.
Figure 2B:
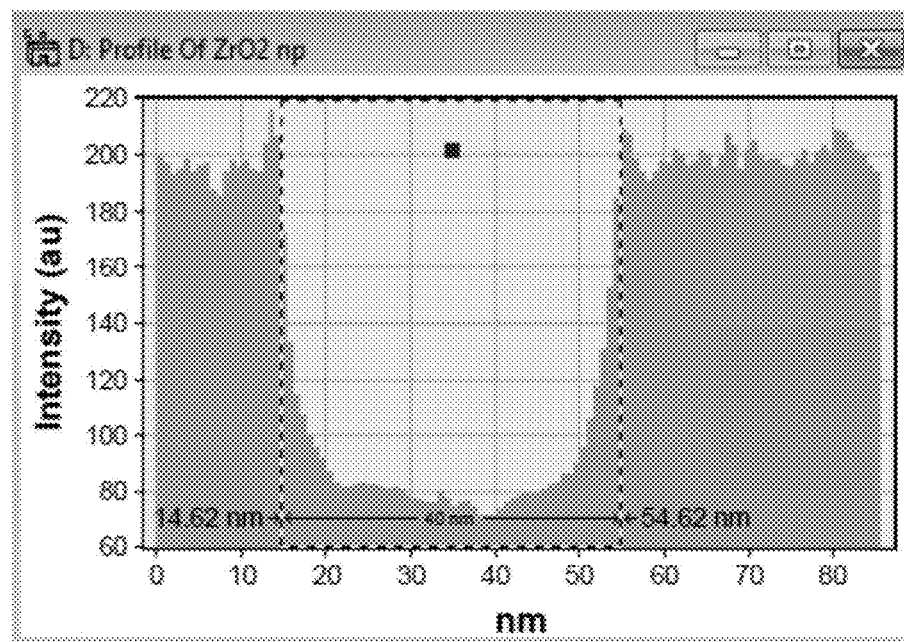
FIG. 2B is an intensity profile taken from the area shown by a white line in one of the nanoparticles in FIG. 2A. The size of this particle was measured to be 40 nm.
Figure 3A:
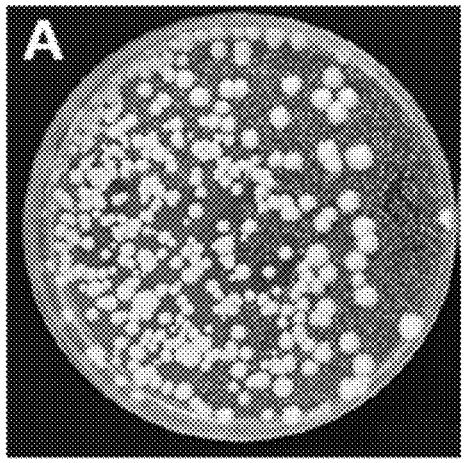
FIG. 3A is a culture count of repair material without $ZrO_2$ nanoparticles and its colonies of *Candida*.
Figure 3B:
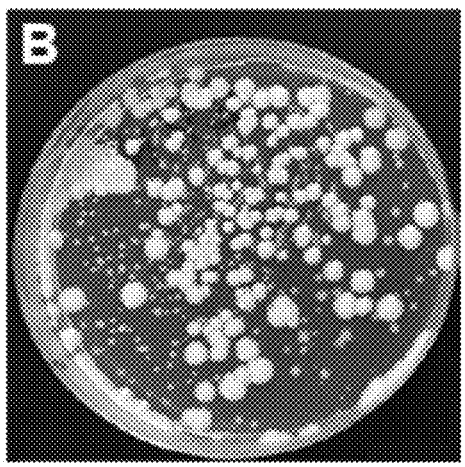
FIG. 3B is a culture count of repair material reinforced with 2.5% w.t. of $ZrO_2$ nanoparticles and its colonies of *Candida*.
Figure 3C:
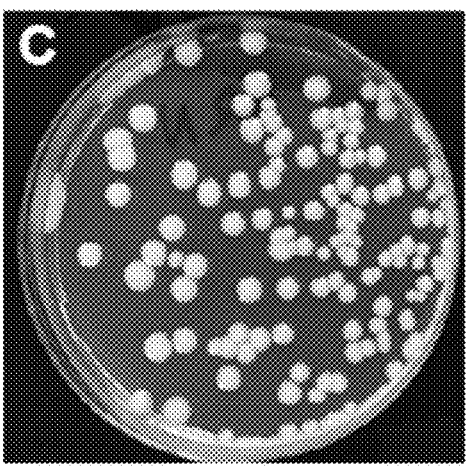
FIG. 3C is a culture count of repair material reinforced with 5% w.t. of $ZrO_2$ nanoparticles and its colonies of *Candida*.
Figure 3D:
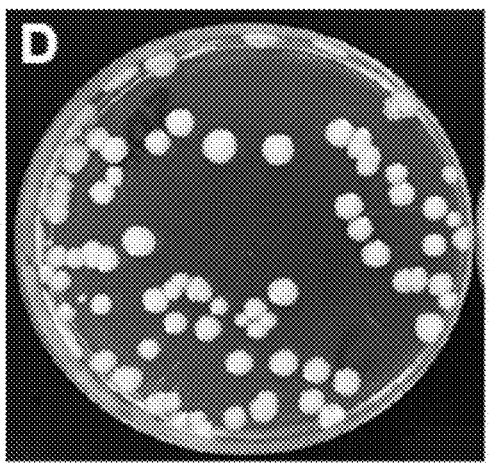
FIG. 3D is a culture count of repair material reinforced with 7.5% w.t. of $ZrO_2$ nanoparticles and its colonies of *Candida*.
Figure 3E:
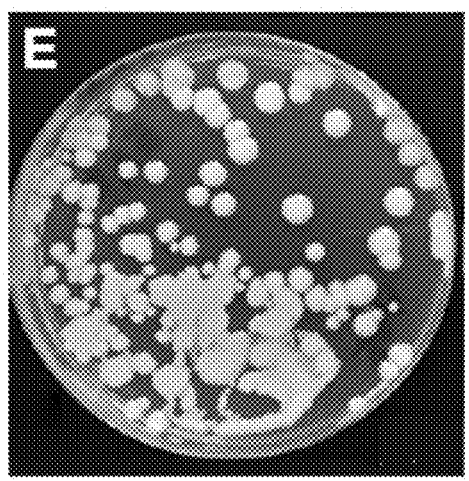
FIG. 3E is a culture count of intact cold-cured acrylic resin without $ZrO_2$ nanoparticles and its colonies of *Candida*.
Figure 3F:
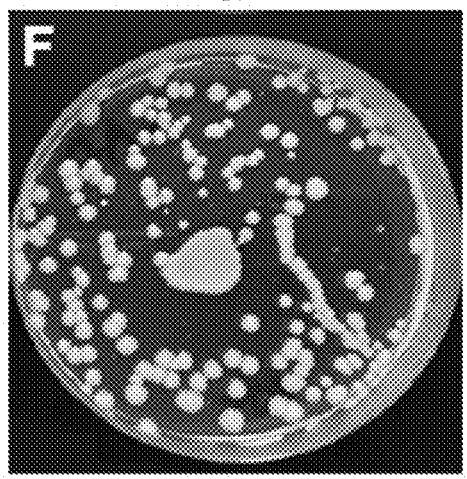
FIG. 3F is a culture count of intact cold-cured acrylic resin reinforced with 2.5% w.t. of $ZrO_2$ nanoparticles and its colonies of *Candida*.
Figure 3G:
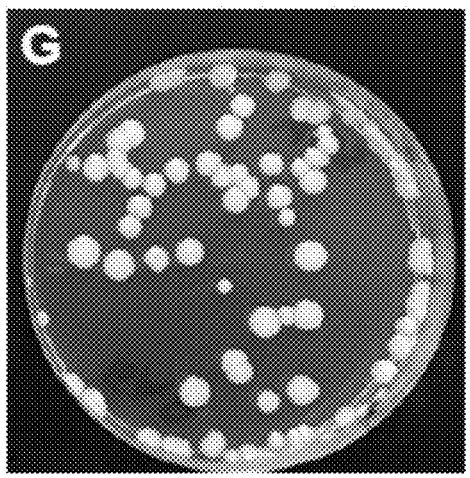
FIG. 3G is a culture count of intact cold-cured acrylic resin reinforced with 5% w.t. of $ZrO_2$ nanoparticles and its colonies of *Candida*.
Figure 3H:
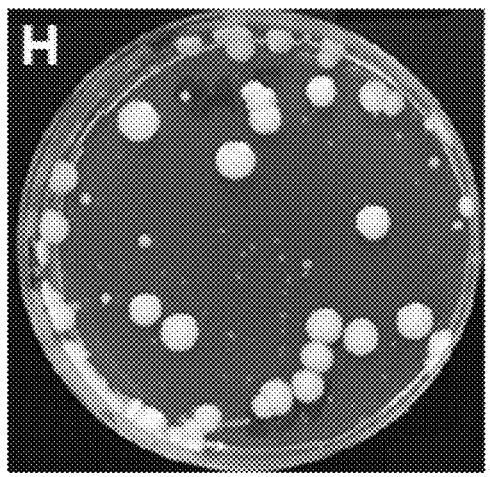
FIG. 3H is a culture count of intact cold-cured acrylic resin reinforced with 7.5% w.t. of $ZrO_2$ nanoparticles and its colonies of *Candida*.

Nano-ZrO$_2$ (99.9%, 100 nm, 1314-23-4; Shanghai Richem International Co., Ltd., Shanghai, China) with a surface area of 9±2 m$^2$/g and an average size of 40±2 nm (FIG. 2) was treated with 0.3 g of silane coupling agent 3-(trimethoxysilyl)propyl methacrylate (TMSPM; Shanghai Richem International Co., Ltd.). This process allows for adequate adhesion between the resin matrix and zirconia nanoparticles. The treated nano-ZrO$_2$ were weighed; prepared in concentrations of 0% wt, 2.5% wt, 5% wt, or 7.5% wt of cold-cured acrylic resin powder (Major.Repair; Major Prodotti Dentari SPA); mixed using a mortar and pestle, and then stirred for 30 min to achieve an even distribution of particles and to obtain a consistent and uniform color.

iii. Repair Procedures

The heat-polymerized specimens in each of the four groups (n=60) were sectioned at the center. A line was drawn 1 mm along and parallel to the cutting edge on both sides. Then, the marked areas were removed using a diamond disk, creating a 2 mm repair gap. The sectioned parts were assembled into the original mold and fixed to create a 2 mm repair gap. According to the manufacturer's recommendations, the mixed nanocomposite powder was dispersed in a methyl methacrylate monomer with a powder/liquid mass ratio of 2:1; then, the subsequent material was mixed and packed into the repair area, adding an excess amount to compensate for polymerization shrinkage (Table 1). The polymer slightly overfilled the repair gap to compensate for polymerization shrinkage and finishing procedures. Once the surface of the repair material lost its glaze, the molds and their contents were placed in a pressure chamber containing 40° C. water at a pressure of 30 lb/inch$^2$ (pound-force per square inch) for 15 minutes. After polymerization was completed, the specimens were taken out of the molds and excess resins were trimmed. Finishing and polishing procedures were carried out using a tungsten carbide bur (HM251FX-040-HP; Meisinger) and acrylic polisher (HM251 FX-060; Meisinger) for all specimens' surfaces except for the intaglio surface (tissue-side surface). Polished specimens were ultrasonically cleaned, placed in distilled water, incubated at 37'C for 1 week and then subjected to the microbiology test.

iv. Preparation of Intact Cold-Cured Specimens

A total of 60 standard nano-ZrO$_2$-reinforced cold-cured acrylic resin specimens were prepared in different concentrations of nano-ZrO$_2$ particles (Table 1 and FIG. 1D). Nano-ZrO$_2$-reinforced cold-cured acrylic powder was mixed with monomer and packed directly into the molds. Once the surface of the repair material lost its glaze, the molds and their contents were placed in a pressure chamber containing 40° C. water at a pressure of 30 lb/inch$^2$ for 15 minutes. After curing, the specimens were removed from the molds, finished, polished (except the intaglio surface) as the repaired group, and subjected to the same microbiology test as the groups of repaired specimens.

Example 2

Microbiology Test i. Exposing Acrylic Specimens to *C. Albicans*

All specimens of acrylic plates were immersed in artificial saliva containing 2,000,000 cells of *C. albicans* (ATCC 10231) and then incubated for 48 hours at 37° C. After that, specimens were washed three times with phosphate-buffered saline, where the number of *C. albicans* proliferated and attached to the surface of the acrylic resin specimens and were subjected to the evaluation process.

ii. Evaluation

Two methods were used to calculate the number of living *C. albicans* adhering to the acrylic resin specimens after the following preparation: plates were incubated for 48 hours in a broth at 37° C. after washing each specimen with phosphate-buffered saline; they were then vibrated using a vortex, followed by tubes centrifuging with the plates to obtain a concentrated bullet of *Candida*. At this step, two methods of counting were used for each sample:

1. Slide count: each specimen was placed on a slide counter (Neubauer slide counter with chambers, "Marienfeld") after adding 2.5 μL of Trypan Blue 0.4% solution in phosphate (Mp Biomedical, Santa Ana, Calif., USA) to 7.5 μL of each sample for microscopic evaluation. Trypan Blue stain was used to differentiate between dead and living *C. albicans*; living *Candida* appeared transparent with a blue borderline, while dead *C. albicans* appeared blue in color. To count the number of *Candida*, a light microscope at a low power magnification (10×) was used. The slide count contained four main squares; each was divided into 16 squares.

*C. albicans* was counted in two main squares and then was multiplied by 2 to estimate the total number of *Candida* on the slide.

2. Direct culture method: In all, 10 μL of each centrifuged bullet was taken and spread on a petri dish. It was then incubated for 24 hours at 37° C. A marker pen counter (colony counter "SP Scienceware, Bel-Art Products") was used to count the colonies of *C. albicans*. The numbers of colonies were corrected for the dilution factor. When the numbers of colonies reached ≥500, it was considered overgrowth.

iii. Statistical Analysis

SPSS 20.0 (IBM Corporation, Armonk, N.Y., USA) was used to run the statistical data analysis. The results of the *Candida* count with two different methods were represented as arithmetic mean and standard deviation (SD). All variables were checked for normality using the Shapiro-Wilk test. Multivariate analysis of variance (MANOVA) was applied to compare the mean effect on each interval with the baseline in a vertical direction (intragroup) and to compare between two methods in a horizontal direction (intergroup). Post hoc Tukey's HSD test was performed to compare the difference of means between the observations taken at various intervals with the baseline. If the P-value was ≤0.05, it was considered as statistically significantly different.

Example 3

Results

Prevention of DS could be achieved by preventing or at least reducing *Candida* adhesion to denture surfaces. Therefore, more research related to denture materials and focusing on ways to reduce the adhesion of biofilms is needed. Such research may be effective in decreasing yeast and bacterial colonization, which could assist in the potential reduction in DS. Many studies have investigated the role of modified denture surfaces in decreasing the adhesion of *C. albicans* and minimizing the formulation of biofilms on denture surfaces. Most of the previous studies concentrated on polishing and smoothing the different denture base materials and adding antimicrobial reinforcement material, such as nanosilver. However, the antibacterial impact of zirconia nanoparticles (nano-$ZrO_2$) against *C. albicans* has not been well addressed. Therefore, the current study was conducted to assess the antifungal effect of nano-$ZrO_2$ on the adhesion of *C. albicans* to acrylic resin denture bases repaired with nano-$ZrO_2$-reinforced cold-cured acrylic resin and denture bases made of cold-cured acrylic resins.

i. MANOVA Test

Figure 4:
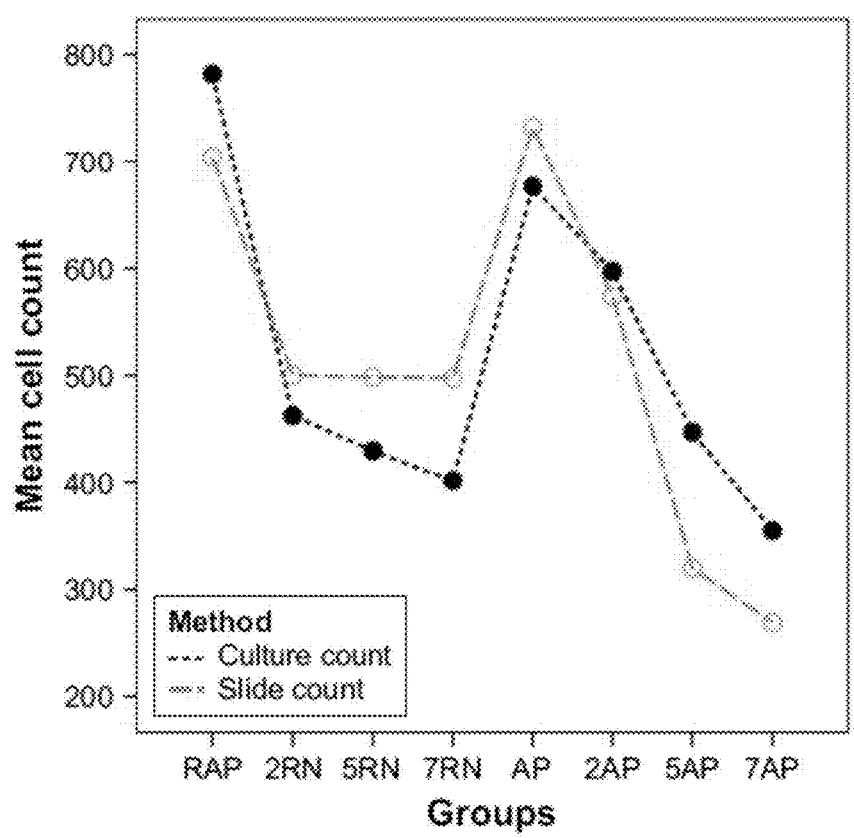
FIG. 4 is a comparison of mean cell counts determined using culture count and slide count methods.

The mean living *Candida* counts for all tested specimen groups were statistically significant among the two test methods, the direct culture test and the slide count (P-values ≤0.0001). Table 2 summarizes the MANOVA test findings across the culture count and slide count methods. The mean difference between the two tested methods regarding the number of living *C. albicans* is illustrated in FIGS. 3 and 4.

TABLE 2

Mean, SD, and MANOVA test results of live *Candida* count for both test methods

| Code | Culture count (mean ± SD) | Slide count (mean ± SD) | n | F | P-value |
|---|---|---|---|---|---|
| RAP | 782.00 ± 14.407 | 704.30 ± 12.859 | 15 | 161.9 | <0.0001* |
| 2RN | 462.40 ± 10.617 | 500.20 ± 11.084 | 15 | 60.66 | <0.0001* |
| 5RN | 429.70 ± 7.056 | 498.40 ± 8.140 | 15 | 406.7 | <0.0001* |
| 7RN | 401.60 ± 8.181 | 497.40 ± 6.077 | 15 | 883.6 | <0.0001* |
| AP | 676.40 ± 15.364 | 732.40 ± 11.530 | 15 | 85.0 | <0.0001* |
| 2AP | 597.30 ± 10.935 | 573.70 ± 10.350 | 15 | 24.6 | <0.0001* |
| 5AP | 446.90 ± 10.713 | 320.10 ± 16.408 | 15 | 418.7 | <0.0001* |
| 7AP | 355.10 ± 40.289 | 269.00 ± 9.752 | 15 | 43.1 | <0.0001* |

Notes:
*Significant difference among the observations taken on various intervals compared to the baseline at α = 0.01 level of significance. Description of the groups is presented in Table 1.
Abbreviations:
SD, standard deviation;
MANOVA, multivariate analysis of variance.

ii. Direct Culture Method

A culture test was also performed to count the number of living *Candida* (FIGS. 3 and 4), and an SD at 95% CI was calculated for each group. Variations of living *Candida* for each group, compared with the baseline group, were checked for statistical significance in a linear manner. An analysis of variance (ANOVA) test was used that found that, for baseline repaired specimens, the mean living *Candida* count was significantly higher than all tested groups following the addition of nano-$ZrO_2$ fillers. As the concentration of nano-$ZrO_2$ increased, the *Candida* count significantly decreased in comparison with RAP (P-values<0.001). 7RN had the lowest living *Candida* counts among their designated groups with a mean value of 401.6. Table 3 summarizes the ANOVA findings for the repaired specimens. Similarly, the intact cold-cured groups showed a significant difference between the unreinforced intact cold-cured groups and nano-$ZrO_2$-reinforced groups (P-values <0.01). Once again, the mean living *Candida* count significantly decreased as nano-$ZrO_2$ concentrations increased. 7AP showed the lowest living *Candida* count with a mean value of 355.1. Table 4 summarizes the ANOVA findings for the intact cold-cured specimens using the direct culture method. To further analyze the differences between the groups, a post hoc analysis found that all groups were significantly different using the culture count method (P-values <0.01).

TABLE 3

ANOVA test for association between live *Candida* count for both test methods and the percentage of $ZrO_2$ by weight for RN

| Variable | Mean ± SD | 95% CI | | F | ANOVA, p-value | Comparison group | Post hoc |
|---|---|---|---|---|---|---|---|
| Culture count | | | | 4,308.02 | <0.001* | | |
| RAP | 782.00 ± 14.407 | 771.7 | 792.3 | | | RAP vs 2RN | 0.005* |
| 2RN | 462.40 ± 10.617 | 454.8 | 470.0 | | | RAP vs 5RN | 0.005* |
| | | | | | | RAP vs 7RN | 0.005* |

TABLE 3-continued

ANOVA test for association between live *Candida* count for both test methods and the percentage of $ZrO_2$ by weight for RN

| Variable | Mean ± SD | 95% CI | | F | ANOVA, p-value | Comparison group | Post hoc |
|---|---|---|---|---|---|---|---|
| 5RN | 429.70 ± 7.056 | 424.7 | 434.7 | | | 2RN vs 5RN | 0.005* |
| | | | | | | 2RN vs 7RN | 0.005* |
| 7RN | 401.60 ± 8.181 | 395.7 | 407.4 | | | 5RN vs 7RN | 0.005* |
| Slide count | | | | 1,620.74 | <0.001* | | |
| RAP | 704.30 ± 12.859 | 695.1 | 713.5 | | | RAP vs 2RN | 0.005* |
| 2RN | 500.20 ± 11.084 | 492.3 | 508.1 | | | RAP vs 5RN | 0.005* |
| | | | | | | RAP vs 7RN | 0.005* |
| 5RN | 498.40 ± 8.140 | 492.6 | 504.2 | | | 2RN vs 5RN | 0.859* |
| | | | | | | 2RN vs 7RN | 0.415* |
| 7RN | 497.40 ± 6.077 | 493.1 | 501.7 | | | 5RN vs 7RN | 0.574* |

Notes:
All tests were performed at a significance level of $\alpha = 0.05$.
*Significant at $P < 0.01$.
Description of the groups is presented in Table 1.
Abbreviations:
SD, standard deviation;
ANOVA, analysis of variance.

TABLE 4

ANOVA test for association between live *Candida* count for both test methods and the percentage of $ZrO_2$ by weight for AP

| Variable | Mean ± SD | 95% CI | | F | ANOVA, p-value | Comparison group | Post hoc |
|---|---|---|---|---|---|---|---|
| Culture count | | | | 601.52 | 0.001* | | |
| AP | 676.40 ± 15.364 | 665.4 | 687.4 | | | AP vs 2AP | 0.005* |
| 2AP | 597.30 ± 10.935 | 589.5 | 605.1 | | | AP vs 5AP | 0.005* |
| | | | | | | AP vs 7AP | 0.005* |
| 5AP | 446.90 ± 10.713 | 439.2 | 454.6 | | | 2AP vs 5AP | 0.005* |
| | | | | | | 2AP vs 7AP | 0.005* |
| 7AP | 355.10 ± 40.289 | 383.9 | 383.9 | | | 5AP vs 7AP | 0.007* |
| Slide count | | | | 4,712.9 | 0.001* | | |
| AP | 732.40 ± 12.859 | 724.1 | 740.6 | | | AP vs 2AP | 0.005* |
| 2AP | 573.70 ± 10.350 | 566.3 | 581.1 | | | AP vs 5AP | 0.005* |
| | | | | | | AP vs 7AP | 0.005* |
| 5AP | 320.10 ± 16.408 | 308.4 | 331.8 | | | 2RN vs 5RN | 0.005* |
| | | | | | | 2RN vs 7RN | 0.005* |
| 7AP | 269.00 ± 9.752 | 262.0 | 276.0 | | | 5RN vs 7RN | 0.005* |

Notes:
All tests were performed at a significance level of $\alpha = 0.05$.
*Significant at $P < 0.01$.
Description of the groups is presented in Table 1.
Abbreviations: ANOVA, analysis of variance: SD, standard deviation.

iii. Slide Count

Using the light microscope, it was shown that the mean numbers of counted living *C. albicans* for baseline groups were significantly higher than those for the nano-$ZrO_2$-reinforced groups. Within the repaired groups, RAP, 2RN, 5RN, and 7RN, a statistically significant difference was observed (P-values <0.01). The post hoc analysis revealed that only the baseline RAP group was significantly different from the other groups (P-values <0.01). However, the 2RN, 5RN, and 7RN groups were not statistically different. Table 3 summarizes the ANOVA and post hoc findings for the repaired specimens using the slide count method. Among the intact cold-cured group, it was found that this variation in living *Candida* between the unreinforced group and the nano-$ZrO_2$-reinforced group was significantly different (P-values <0.01). As the concentrations of nano-$ZrO_2$ increased, the mean slide count of *Candida* decreased. The differences between the groups were statistically significant (P-values <0.01). The 7AP group had the lowest mean *Candida* count value at 269. Table 4 summarizes the ANOVA findings for the intact cold-cured specimens using the culture count.

It was found in this study that nano-$ZrO_2$ could have an antifungal effect on both the repaired denture base and intact cold-cured resins. The significant difference in the reduction of the number of *C. albicans* was observed with the addition of 7.5% nano-$ZrO_2$ using both tested methods. This result indicated that nano-$ZrO_2$ can be an effective material in the creation of an antimicrobial medium against *C. albicans*.

iv. Transmission Electron Microscopy (TEM) Results of Nano-$ZrO_2$

TEM was performed to estimate the size of nano-$ZrO_2$ (FIG. 1A). Several such images were taken to measure the average size of the particles. The size of different particles was measured by extracting the intensity profiles as shown in FIG. 1B. This intensity profile was taken from the area (having a particle) shown by a white line. The size of this particle was measured to be ~40 nm. The average size of the particle was estimated to be ~40±2 nm and the SD to be ~11 nm. In all, >80 particles were taken for this measurement.

v. Scanning Electron Microscopy (SEM) for Specimen Surface Analysis

Figure 5A:
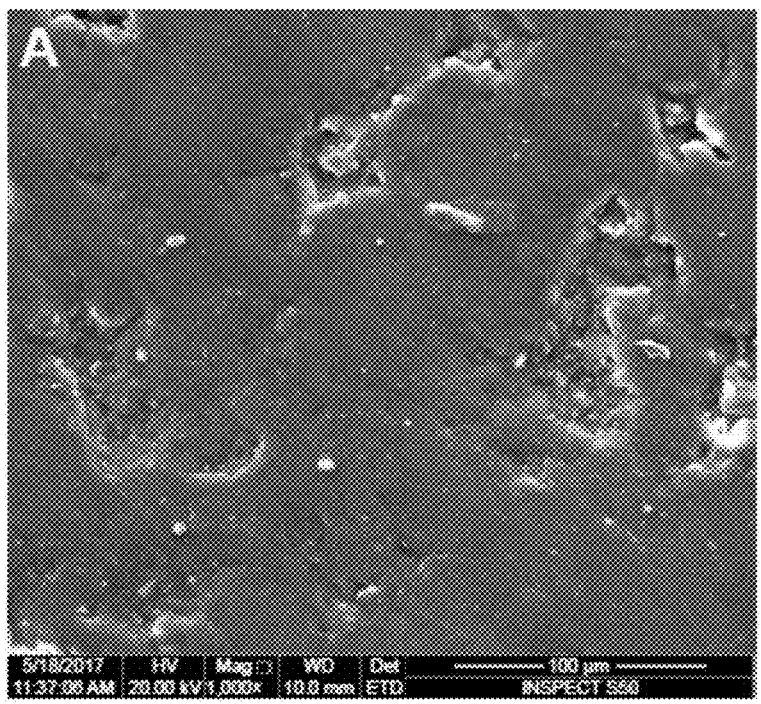
FIG. 5A is a representative SEM image for cold-cured acrylic resin without $ZrO_2$ nanoparticles (low magnification, 1,000×).
Figure 5B:
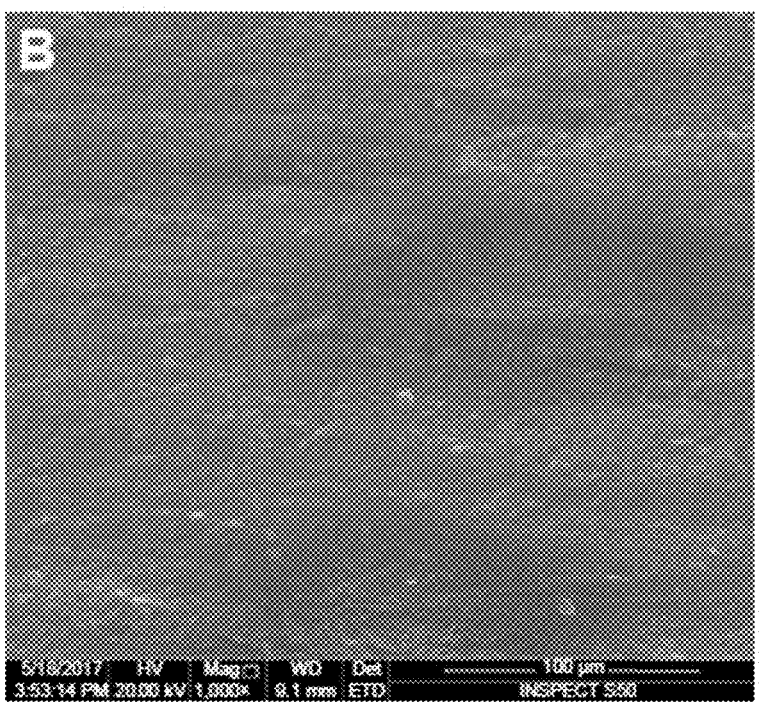
FIG. 5B is a representative SEM image for cold-cured acrylic resin with $ZrO_2$ nanoparticles (low magnification, 1,000×).
Figure 5C:
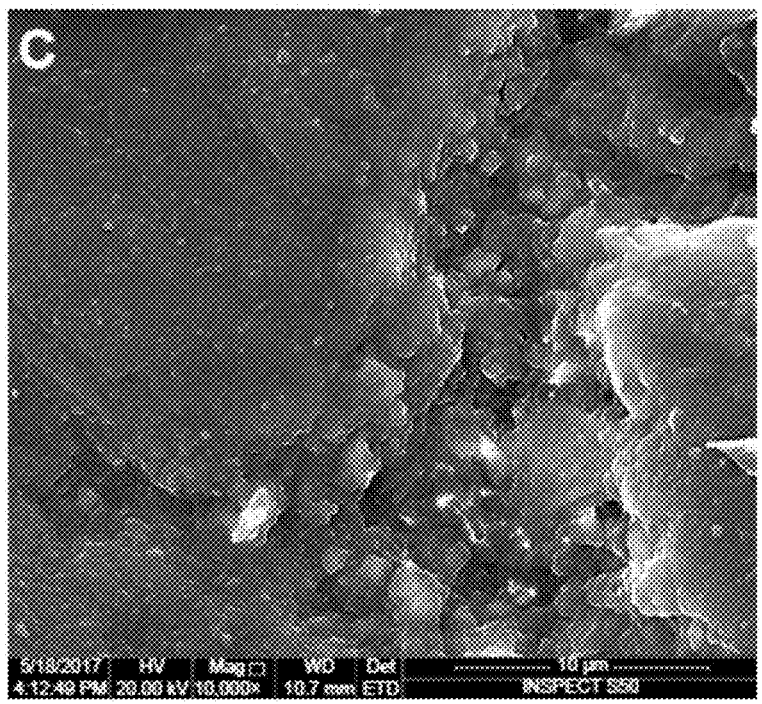
FIG. 5C is a representative SEM image for cold-cured acrylic resin without $ZrO_2$ nanoparticles (high magnification, 10,000×).
Figure 5D:
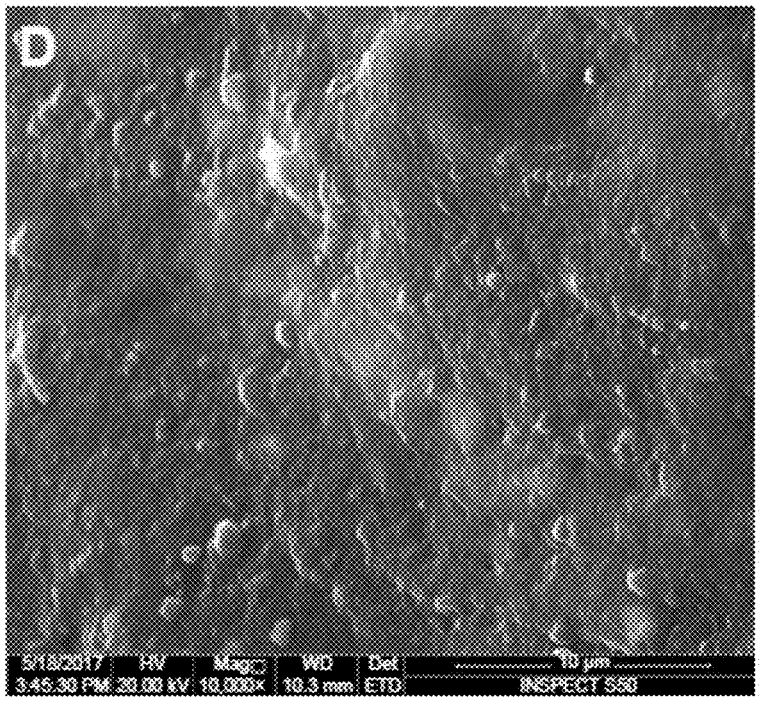
FIG. 5D is a representative SEM image for cold-cured acrylic resin with $ZrO_2$ nanoparticles (high magnification, 10,000×).

SEM analyses showed high surface roughness in unreinforced cold-cured acrylic resin (FIGS. 5A and 5C), while the addition of nano-$ZrO_2$ exhibited smooth surface in addition to the presence of nanoparticles on the resin surfaces (FIGS. 5B and 5D).

In the current study, the mean number of colonies of *C. albicans* in the tested groups decreased compared with the control group. These drawbacks of cold polymerization may be explained by the chemical initiator that reduces the conversion degree during the polymerization stage and disrupts the surface structure. These statements are consistent with the results of the current study that the cold-cured group represented high colony numbers. This may be due to the surface roughness of this repairing material. It is well known that microbial adherence is highly affected by surface roughness. Basically, resin roughness and voids in the fitting surface of denture base acrylic enhance the initial microbial adhesion.

The findings of the present study indicated that repair acrylic resin reinforced with nano-$ZrO_2$ significantly reduced the microbial counts. The addition of nano-$ZrO_2$ to repair resin resulted in a significant decrease in *C. albicans* count, and the maximum decrease was found with the addition of 7.5% of nano-$ZrO_2$. This decrease in the colony number may be attributed to the antimicrobial activity of nano-$ZrO_2$ or its potential effect in improving surface properties. The antimicrobial effect of nano-$ZrO_2$ was reported by Jangra et al (Jangra S L, Stalin L, Dilbaghi N, et al. Antimicrobial activity of zirconia ($ZrO_2$) nanoparticles and zirconium complexes. *J Nanosci Nanotechnol.* 2012, 12(9), 7105-7112, incorporated herein by reference in its entirety) who found that nano-$ZrO_2$ worked preliminarily on the bacterial strains of *E. coli* and *S. aureus* and on the fungal strain of *A. niger* and mainly showed activity against only *E. coli*. Some studies showed that nano-$ZrO_2$ fills polymeric chain spaces and spaces on the surface, as its proper bonding to the polymer matrix resulted in smooth surfaces, which could prevent *C. albicans* adhesion. Owing to the double effect of nano-$ZrO_2$ (antimicrobial and surface texture changes; FIGS. 5B and D), this investigation might have an impact in minimizing the adhesion of *C. albicans* in relation to DS development.

Nano-$ZrO_2$ may actively inhibit the growth of fungal strains by interfering in cell function and causing deformation in fungal hyphae (Gowri S, Rajiv Gandhi R, Sundrarajan M. Structural, optical, antibacterial and antifungal properties of zirconia nanoparticles by biobased protocol. *J Mater Sci Technol.* 2014, 30(8), 782-790, incorporated herein by reference in its entirety). Another explanation could be that the differences in antibacterial activity of nano-$ZrO_2$ against *S. aureus* and *E. coli* could be attributed to the surface charge. Generally, it is believed that chemical reactivation of crystals may be significantly affected by their shapes, due to the surface energy, surface atom arrangement, and bonding (Wang X, Wu H F, Kuang Q, Huang R B, Xie Z X, Zheng L S. Shape-dependent antibacterial activities of $Ag_2O$ polyhedral particles. *Langmuir* 2010, 26(4), 2774-2778, incorporated herein by reference in its entirety). Different atomic planes have different surface energies, where the density of the dangling bonds on the surface dominates the contribution to the surface energy of nanostructures. This difference in surface energy plays a crucial role in defining the antibacterial and antifungal properties of nanostructured inorganic materials (Wang X, Yang F, Yang W, Yang X. A study on the antibacterial activity of one-dimensional ZnO nanowire arrays: effects of the orientation and plane surface. *Chem. Commun.* 2007, 42, 4419-4421; and Park S E, Blissett R, Susarla S M, Weber H P. *Candida albicans* adherence to surface-modified denture resin surfaces. *J Prosthodont.* 2008, 17(5), 365-369, each incorporated herein by reference in their entirety). Additionally, it could be speculated that the nano-$ZrO_2$ has the same surface geometry, but with different shapes, different active facets may exhibit different antimicrobial activities.

Based on the results of the current study, significant differences were found between reinforced cold-cured acrylic resin and the control group. Moreover, significant differences were found between reinforced cold-cured acrylic resin as nano-$ZrO_2$ concentration increased, which confirmed the potential effect of nano-$ZrO_2$ in the prevention of *Candida* adhesion (FIG. 3).

In comparing the repair and intact cold-cured groups, the intact groups demonstrated fewer colony numbers with the same percentage of nano-$ZrO_2$. This finding raised another factor that could affect *Candida* adhesions and that may be related to different resin types or the joints between the denture base and repair resin. These joints may act as a reservoir for *C. albicans*, particularly if they are not prepared properly.

From a clinical point of view, the results of this study have been interpreted with caution because the environment of the oral cavity is dynamic. Multiple factors, including pH, the presence of different microorganisms, and saliva, can affect the microbial adhesion to the denture surface (Ferreira M A, Pereira-Cenci T, Rodrigues L M, Rodrigues-Garcia R C, Del Bel Cury A A. Efficacy of denture cleansers on denture liners contaminated with *Candida* species. *Clin Oral Investig.* 2009, 13(2), 237-242, and Al-Thobity A M, Al-Khalifa K S, Gad M M, Al-Hariri M, Ali A A, Alnassar T. In vitro evaluation of the inhibitory activity of thymoquinone in combatting *Candida albicans* in denture stomatitis prevention. *Int J Environ Res Public Health.* 2017, 14(7), 743, each incorporated herein by reference in their entirety). Clinical implications of this study include that nano-$ZrO_2$ could be added to repair resin due to its potential effect on reducing and preventing adhesion and proliferation of *Candida*. Additionally, cold-cured removable prostheses could be fabricated with the addition of nano-$ZrO_2$. Moreover, the addition of nano-$ZrO_2$ to an acrylic denture base could increase the antifungal activity while maintaining adequate mechanical properties for clinical use. Therefore, further investigation into the antifungal effect of denture base material reinforced with nano-$ZrO_2$ is required. Moreover, the durability of these nanocomposites is of importance, because it could help complete-denture wearers who have restricted manual proficiency or cognitive disorders to improve their denture hygiene status.

In conclusion, within the limitations of this study, we can conclude that repair acrylic resin modified with nano-$ZrO_2$ could exhibit antifungal effects on *C. albicans* and could be used for the prevention of DS by preventing *Candida* adhesion. Adding zirconia nanoparticles to cold-cured resin could be an effective method to reduce the adhesion of *C. albicans* on surfaces of PMMA interim prostheses.

The invention claimed is:

1. A method of preventing or treating an oral infection in a subject by preventing or reducing adhesion of a microorganism to a repaired acrylic dental appliance worn by the subject, the method comprising:

dispersing a nanocomposite powder in a monomer liquid comprising methyl methacrylate thereby forming a reinforcement resin, the nanocomposite powder comprising:
- an acrylic polymer powder comprising polymethyl methacrylate; and
- zirconium dioxide nanoparticles;

applying and packing the reinforcement resin in excess to a repair gap of an acrylic dental appliance; and autopolymerizing the reinforcement resin thereby forming the repaired acrylic dental appliance.

2. The method of claim 1, wherein the microorganism is selected from the group consisting of bacteria and fungi.

3. The method of claim 1, wherein the microorganism is a fungus selected from the *Candida* species.

4. The method of claim 1, wherein the nanocomposite powder comprises 1-10 wt % zirconium dioxide nanoparticles relative to a total weight of the nanocomposite powder.

5. The method of claim 1, wherein the zirconium dioxide nanoparticles have an average size of 20-110 nm, and an average surface area of 5-15 $m^2/g$.

6. The method of claim 1, wherein the reinforcement resin has a nanocomposite powder to monomer liquid mass ratio in a range of 0.5:1 to 3:1.

7. The method of claim 1, wherein the autopolymerizing is performed at a temperature of 20-50° C., and a pressure of 10-50 psi.

8. The method of claim 1, further comprising treating the zirconium dioxide nanoparticles with a silane coupling reagent prior to the dispersing.

9. The method of claim 1, wherein reduced adhesion of the microorganism to the repaired acrylic dental appliance is measurable by a microbial count.

10. The method of claim 1, wherein the acrylic dental appliance is a denture.

11. The method of claim 1, wherein the oral infection is denture stomatitis.

* * * * *